(12) United States Patent
Cronin et al.

(10) Patent No.: US 9,907,613 B2
(45) Date of Patent: *Mar. 6, 2018

(54) RADIATION APPLICATOR AND METHOD OF RADIATING TISSUE

(71) Applicant: AngioDynamics, Inc., Latham, NY (US)

(72) Inventors: Nigel Cronin, Lane Bath (GB); Maria J Boix, Bath (GB)

(73) Assignee: AngioDynamics, Inc., Latham, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/940,354

(22) Filed: Nov. 13, 2015

(65) Prior Publication Data

US 2016/0262832 A1 Sep. 15, 2016

Related U.S. Application Data

(62) Division of application No. 10/577,414, filed on Apr. 26, 2006, now Pat. No. 9,788,896.

(30) Foreign Application Priority Data

| Jul. 1, 2005 | (EP) | PCT/EP2005/007103 |
| Jan. 3, 2006 | (GB) | 600018.6 |

(51) Int. Cl.
*A61B 18/18* (2006.01)
*A61B 18/04* (2006.01)
(Continued)

(52) U.S. Cl.
CPC ......... *A61B 18/1815* (2013.01); *A61B 18/04* (2013.01); *A61B 18/18* (2013.01);
(Continued)

(58) Field of Classification Search
CPC ...... A61B 2018/1838; A61B 2018/183; A61B 18/1815; A61B 18/18
See application file for complete search history.

(56) References Cited

U.S. PATENT DOCUMENTS

| 3,461,261 A | 8/1969 | Lewis et al. |
| 3,871,359 A | 3/1975 | Allan |

(Continued)

FOREIGN PATENT DOCUMENTS

| EP | 0294854 A2 | 12/1988 |
| GB | 2074826 A | 11/1981 |

(Continued)

OTHER PUBLICATIONS

Maybody, An Overview of Image-Guided Percutaneous Ablation of Renal Tumors, Seminars in Interventional Radiology/vol. 27, No. 3, 2010, pp. 261-267.

(Continued)

*Primary Examiner* — Ronald Hupczey, Jr.
(74) *Attorney, Agent, or Firm* — Zachary F. Madonna, Esq.

(57) ABSTRACT

A dipole microwave applicator emits microwave radiation into tissue to be treated. The applicator is formed from a thin coax cable having an inner conductor surrounded by an insulator, which is surrounded by an outer conductor. A portion of the inner conductor extends beyond the insulator and the outer conductor. A ferrule at the end of the outer conductor has a step and a sleeve that surrounds a portion of the extended inner conductor. A tuning washer is attached to the end of the extended inner conductor. A dielectric tip encloses the tuning washer, the extended inner conductor, and the sleeve of the ferrule. The sleeve of the ferrule and the extended inner conductor operate as the two arms of the dipole microwave antenna. The tuning washer faces the step (Continued)

in the ferrule, and is sized and shaped to cooperate with the step in balancing and tuning the applicator.

20 Claims, 12 Drawing Sheets

(51) Int. Cl.
*G06T 7/30* (2017.01)
*A61B 18/00* (2006.01)
*A61N 5/04* (2006.01)

(52) U.S. Cl.
CPC ...... *G06T 7/30* (2017.01); *A61B 2018/00023* (2013.01); *A61B 2018/00029* (2013.01); *A61B 2018/00077* (2013.01); *A61B 2018/00083* (2013.01); *A61B 2018/00178* (2013.01); *A61B 2018/00577* (2013.01); *A61B 2018/1838* (2013.01); *A61B 2018/1869* (2013.01); *A61B 2018/1892* (2013.01); *A61N 5/045* (2013.01)

(56) References Cited

U.S. PATENT DOCUMENTS

| | | |
|---|---|---|
| 4,446,874 A | 5/1984 | Vaguine |
| 4,476,363 A | 10/1984 | Berggren et al. |
| 4,612,940 A * | 9/1986 | Kasevich ............... A61B 18/18 219/712 |
| 4,676,258 A | 6/1987 | Inokuchi et al. |
| 3,065,752 A | 7/1989 | Larsen |
| 4,891,483 A | 1/1990 | Kikuchi et al. |
| 5,227,730 A | 7/1993 | King et al. |
| 5,364,392 A | 11/1994 | Warner et al. |
| 5,370,644 A | 12/1994 | Langberg |
| 5,458,597 A | 10/1995 | Edwards et al. |
| 5,536,267 A | 7/1996 | Edwards et al. |
| 5,540,737 A | 7/1996 | Fenn |
| 5,620,479 A | 4/1997 | Diederich |
| 5,630,426 A | 5/1997 | Eggers et al. |
| 5,683,384 A | 11/1997 | Gough et al. |
| 5,728,143 A | 3/1998 | Gough et al. |
| 5,735,847 A | 4/1998 | Gough et al. |
| 5,800,484 A | 9/1998 | Gough et al. |
| 5,807,272 A | 9/1998 | Kun et al. |
| 5,810,742 A | 9/1998 | Pearlman |
| 5,810,804 A * | 9/1998 | Gough ............... A61B 18/1477 604/22 |
| 5,873,849 A | 2/1999 | Bernard |
| 6,009,347 A | 12/1999 | Hofmann |
| 6,016,452 A | 1/2000 | Kasevich |
| 6,027,502 A | 2/2000 | Desai |
| 6,050,994 A | 4/2000 | Sherman |
| 6,066,134 A | 5/2000 | Eggers et al. |
| 6,106,524 A | 8/2000 | Eggers et al. |
| 6,134,460 A | 10/2000 | Chance |
| 6,134,476 A | 10/2000 | Arndt et al. |
| 6,200,314 B1 | 3/2001 | Sherman |
| 6,223,085 B1 * | 4/2001 | Dann ............... A61B 18/1492 606/29 |
| 6,223,086 B1 | 4/2001 | Carl et al. |
| 6,287,302 B1 | 9/2001 | Berube |
| 6,296,636 B1 | 10/2001 | Cheng et al. |
| 6,298,726 B1 | 10/2001 | Adachi et al. |
| 6,436,072 B1 | 8/2002 | Kullas et al. |
| 6,478,793 B1 | 11/2002 | Cosman et al. |
| 6,485,487 B1 | 11/2002 | Sherman |
| 6,488,678 B2 | 12/2002 | Sherman |
| 6,497,704 B2 | 12/2002 | Ein-Gal |
| 6,558,378 B2 | 5/2003 | Sherman et al. |
| 6,616,657 B2 | 9/2003 | Simpson et al. |
| 6,635,055 B1 | 10/2003 | Cronin |
| 6,673,070 B2 | 1/2004 | Edwards et al. |
| 6,706,040 B2 * | 3/2004 | Mahon ............... A61B 18/18 128/898 |
| 6,712,811 B2 | 3/2004 | Underwood et al. |
| 6,723,094 B1 | 4/2004 | Desinger |
| 6,770,070 B1 | 8/2004 | Balbierz |
| 6,840,935 B2 | 1/2005 | Lee |
| 6,869,430 B2 | 3/2005 | Balbierz et al. |
| 6,962,587 B2 | 11/2005 | Johnson et al. |
| 7,008,421 B2 | 3/2006 | Daniel et al. |
| 7,311,703 B2 * | 12/2007 | Turovskiy ............... A61B 18/18 606/33 |
| 2002/0077627 A1 | 6/2002 | Johnson et al. |
| 2002/0161361 A1 | 10/2002 | Sherman et al. |
| 2003/0100894 A1 | 5/2003 | Mahon et al. |
| 2003/0109862 A1 | 6/2003 | Prakash et al. |
| 2004/0204679 A1 | 10/2004 | Visconti et al. |
| 2004/0215185 A1 | 10/2004 | Truckai et al. |
| 2004/0267340 A1 | 12/2004 | Cioanta et al. |
| 2005/0015081 A1 | 1/2005 | Turovskiy et al. |
| 2005/0033276 A1 | 2/2005 | Adachi |
| 2005/0107781 A1 | 5/2005 | Ostrovsky et al. |

FOREIGN PATENT DOCUMENTS

| | | |
|---|---|---|
| GB | 2387544 A | 10/2003 |
| JP | 2002109971 A | 4/2002 |
| WO | WO2006002943 A1 | 1/2006 |

OTHER PUBLICATIONS

Carmi, et al, Combination Percutaneous and Intraarterial Therapy for the Treatment of Hepatocellular Carcinoma: A Review, Semin Intervent Radiol 2010, 27:296-301.
Saldanha, et al, Current Tumor Ablation Technologies: Basic Science and Device Review, Semin Intervent Radiol 2010, 27:247-254.
Kurup, et al, Image-Guided Percutaneous Ablation of Bone and soft Tissue Tumors, Semin Intervent Radiol 2010, 27:276-284.
McCarley, et al, Percutaneous Ablation of Hepatic Tumors, Semin Intervent Radiol 2010, 27: 255-260.
International Search Report PCT-EP-05-007103_ISR dated Nov. 10, 2005.
International Search Report PCT-GB-04-002620_IPRP dated Jul. 21, 2005.
International Search Report PCT-EP-05-007553_ISR dated Apr. 10, 2005.
International Search Report PCT-GB-03-04082_IPER dated Nov. 2, 2004.
International Search Report PCT-US-04-043477_ISR dated Aug. 26, 2005.
International Search Report PCT-GB-03-04082_IPER dated Nov. 12, 2004.
International Search Report PCT-GB-04-002620_ISR dated Oct. 1, 2004.
International Search Report PCT-GB-03-004082_ISR dated Apr. 22, 2004.
International Search Report PCT-GB-00-00682_IPRP dated May 21, 2001.
International Search Report PCT-GB-99-01398_IPER dated Aug. 7, 2000.
International Search Report PCT-GB-00-00682_ISR dated May 24, 2000.
International Search Report PCT-GB-99-001400_ISR dated Mar. 9, 1999.
International Search Report PCT-GB-99-001398_ISR dated Nov. 11, 1999.
International Search Report PCT-GB-99-01400_ISR dated Sep. 3, 1999.
International Search Report PCT-GB-99-01398_ISR dated Sep. 3, 1999.
International Search Report PCT-GB-94-01565_IPER dated Nov. 2, 1995.
International Search Report PCT-GB-94-01565_ISR dated Nov. 28, 1994.

* cited by examiner

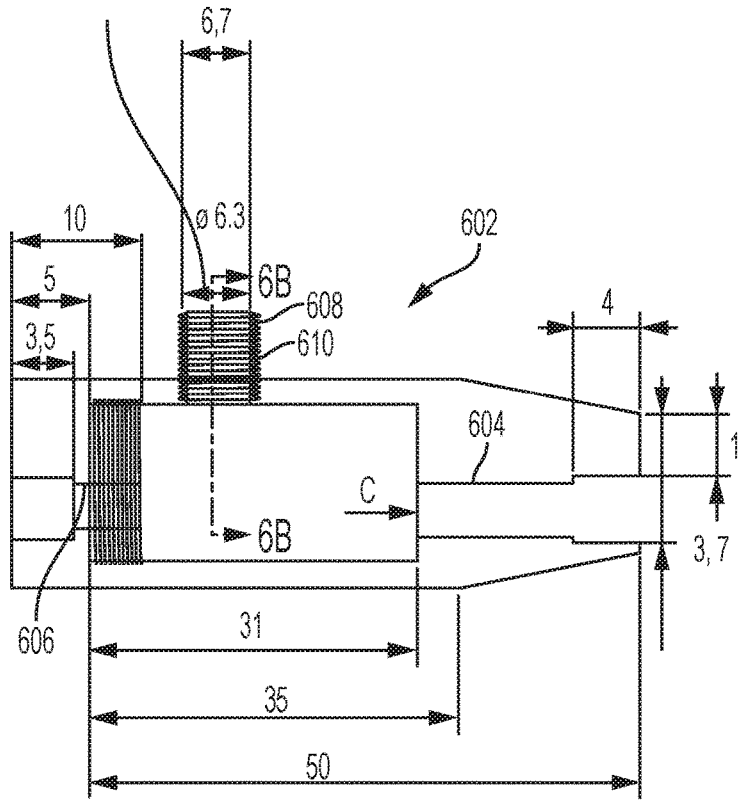
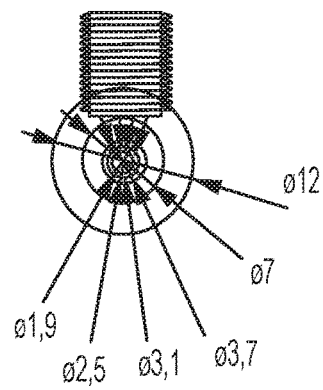
FIG. 6A
FIG. 6B
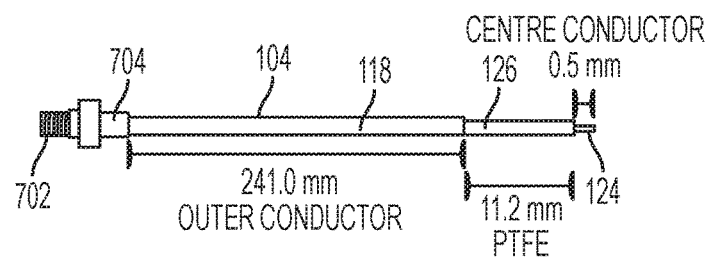
FIG. 7

RADIATION APPLICATOR AND METHOD OF RADIATING TISSUE

CROSS-REFERENCE TO RELATED APPLICATION

This application is a continuation-in-part (CIP) of application Ser. No. 10/577,414 filed Apr. 26, 2006, which in turn is a national stage application of International Application Serial Number PCT/EP2005/007103 filed Jul. 1, 2005.

This application also claims priority to foreign patent application serial number GB0600018.6 filed Jan. 3, 2006.

BACKGROUND OF THE INVENTION

Field of the Invention

The present invention relates generally to medical technology, and more specifically to microwave radiation applicators and methods of thermal ablative treatment of tissue using radiated microwaves.

Background Information

Thermal ablative therapies may be defined as techniques that intentionally decrease body tissue temperature (hypothermia) or intentionally increase body tissue temperature (hyperthermia) to temperatures required for cytotoxic effect, or to other therapeutic temperatures depending on the particular treatment. Microwave thermal ablation relies on the fact that microwaves form part of the electromagnetic spectrum causing heating due to the interaction between water molecules and the microwave radiation. The heat being used as the cytotoxic mechanism. Treatment typically involves the introduction or an applicator into tissue, such as tumors. Microwaves are released from the applicator forming a field around its tip. Heating of the water molecules occurs in the radiated microwave field produced around the applicator, rather than by conduction from the probe itself. Heating is therefore not reliant on conduction through tissues, and cytotoxic temperature levels are reached rapidly.

Microwave thermal ablative techniques are useful in the treatment of tumors of the liver, brain, lung, bones, etc.

U.S. Pat. No. 4,494,539 discloses a surgical operation method using microwaves, characterized in that microwaves are radiated to tissue from a monopole type electrode attached to the tip of a coaxial cable for transmitting microwaves. Coagulation, hemostasis or transaction is then performed on the tissue through the use of the thermal energy generated from the reaction of the microwaves on the tissue. In this way, the tissue can be operated in an easy, safe and bloodless manner. Therefore, the method can be utilized for an operation on a parenchymatous organ having a great blood content or for coagulation or transaction on a parenchymatous tumor. According to the method, there can be performed an operation on liver cancer, which has been conventionally regarded as very difficult. A microwave radiation applicator is also disclosed.

U.S. Pat. No. 6,325,796 discloses a microwave ablation assembly and method, including a relatively thin, elongated probe having a proximal access end, and an opposite distal penetration end adapted to penetrate into tissue. The probe defines an insert passage extending therethrough from the access end to the penetration end thereof. An ablation catheter includes a coaxial transmission line with an antenna device coupled to a distal end of the transmission line for generating an electric field sufficiently strong enough to cause tissue ablation. The coaxial transmission line includes an inner conductor and an outer conductor separated by a dielectric material. A proximal end of the transmission line is coupled to a microwave energy source. The antenna device and the transmission line each have a transverse cross-sectional dimension adapted for sliding receipt through the insert passage while the elongated probe is positioned in the tissue. Such sliding advancement continues until the antenna device is moved to a position beyond the penetration end and further into direct contact with the tissue.

However, a drawback with the existing techniques include the fact that they are not optimally mechanically configured for insertion into and perforation of, the human skin, for delivery to a zone of soft tissue to be treated. Typically, known radiation applicator systems do not have the heightened physical rigidity that is desirable when employing such techniques.

In addition, some radiation applicators made available heretofore do not have radiation emitting elements for creating a microwave field pattern optimized for the treatment of soft tissue tumors.

Also, given the power levels employed in some applicators and treatments, there can be problems of unwanted burning of non-target, healthy tissue due to the very high temperatures reached by the applicator or the components attached thereto.

Further, although small diameter applicators are known, and liquid cooling techniques have been used, there has been difficulty in designing a small diameter device with sufficient cooling in applications employing power levels required to deal with soft tissue tumors.

Accordingly, there is a need for methods of treatment of soft tissue tumors, and for radiation applicators that overcome any or all of the aforementioned problems of the prior art techniques, and provide improved efficacy.

SUMMARY OF THE INVENTION

Briefly, the present invention is directed to a microwave applicator for ablating tissue. The applicator is a dipole microwave antenna that transmits microwave radiation into the tissue being treated. The applicator is formed from a thin coaxial cable having an inner conductor surrounded by an insulator, which is surrounded by an outer conductor or shield. The end of the coaxial cable is trimmed so that a portion of the insulator and inner conductor extend beyond the outer conductor, and a portion of the inner conductor extends beyond the insulator. The applicator further includes a tubular ferrule defining an aperture therethrough. One end of the ferrule is attached to the outer conductor, while the other end, which forms a sleeve, extends out beyond the end of the insulator and around a portion of the extended inner conductor. A step is preferably formed on the outer surface of the ferrule between its two ends. A solid spacer having a central bore to receive the inner conductor abuts an end of the ferrule and surrounds the extended inner conductor. A tuning element is attached to the end of the extended inner conductor, and abuts an end of the spacer opposite the ferrule. The tuning element faces the step in the ferrule, and the step and the tuning element are both sized and shaped to cooperate in balancing and tuning the applicator. A hollow tip, formed from a dielectric material, has an open end and a closed end. The tip encloses the tuning element, the spacer, and the extended inner conductor. The tip also encloses the sleeve of the ferrule, thus defining outer surface of the ferrule that is surrounded by the dielectric tip. The open end of the tip preferably abuts the step in the ferrule. A rigid sleeve surrounds the coaxial cable and extends away from the ferrule opposite the tip. The sleeve, which abuts the step of the ferrule opposite the tip, has an inner diameter that is larger than the coaxial cable, thereby defining an annular space between the outside of the coaxial cable and the inner surface of the sleeve. The sleeve further includes one or more drainage holes, which permit fluid communication between the annular space around the coaxial cable and the outside of the applicator.

In operation, microwave energy from a source is applied to the coaxial cable, and is conveyed to the tip. The portion of the inner conductor that extends beyond the end of the ferrule forms one arm of the dipole, and emits microwave radiation. In addition, the microwave energy flowing along the inner conductor of the coaxial cable and in the aperture of the ferrule induces a current to flow along the outer surface of the sleeve of the ferrule that is surrounded by the tip. This, in turn, causes microwave radiation to be emitted from the sleeve of the ferrule, which operates as the second arm of the dipole. In this way, microwave energy is emitted along a substantial length of the applicator, rather than being focused solely from the tip. By distributing the emission of microwave radiation along a length of the applicator, higher power levels may be employed.

To keep the coaxial cable and the applicator from overheating, a cooling fluid is introduced from a source into the annular space defined by the outside of the coaxial cable and the inside of the sleeve. The cooling fluid flows along this annular space, and absorbs heat from the coaxial cable. The cooling fluid, after having absorbed heat from the coaxial cable, then exits the annular space through the one or more drainage holes in the sleeve, and perfuses adjacent tissue.

The closed end of the tip is preferably formed into a blade or point so that the microwave applicator may be inserted directly into the tissue being treated. The tip, ferrule, and rigid sleeve, moreover, provide strength and stiffness to the applicator, thereby facilitating its insertion into tissue.

The present invention further provides a method of treating target tissue, such tumor, the tumor being formed of, and/or being embedded within, soft tissue. The method includes inserting the microwave applicator into the tumor, and supplying electromagnetic energy to the applicator, thereby radiating electromagnetic energy into the tumor.

BRIEF DESCRIPTION OF THE DRAWINGS

Embodiments of the invention will now be described, by way of example, with reference to the accompanying drawings, in which:

FIG. 6A shows an axial cross-section, and FIG. 6B shows a transverse cross-section of a handle section that may be attached to the radiation applicator of FIG. 1;

FIG. 7 illustrates the portion of coaxial cable that passes through the tube of the radiation applicator of FIG. 1;

DETAILED DESCRIPTION OF AN ILLUSTRATIVE EMBODIMENT

In the following description, like references are used to denote like elements, and where dimensions are given, they are in millimeters (mm). Further, it will be appreciated by persons skilled in the art that the electronic systems employed in accordance with the present invention, to generate, deliver and control the application of radiation to parts of the human body may be as described in the art heretofore. In particular, such systems as are described in commonly owned published international patent applications WO95/04385, WO99/56642 and WOOO/49957 may be employed (except with the modifications described hereinafter). Full details of these systems have been omitted from the following for the sake of brevity.

Figure 1:
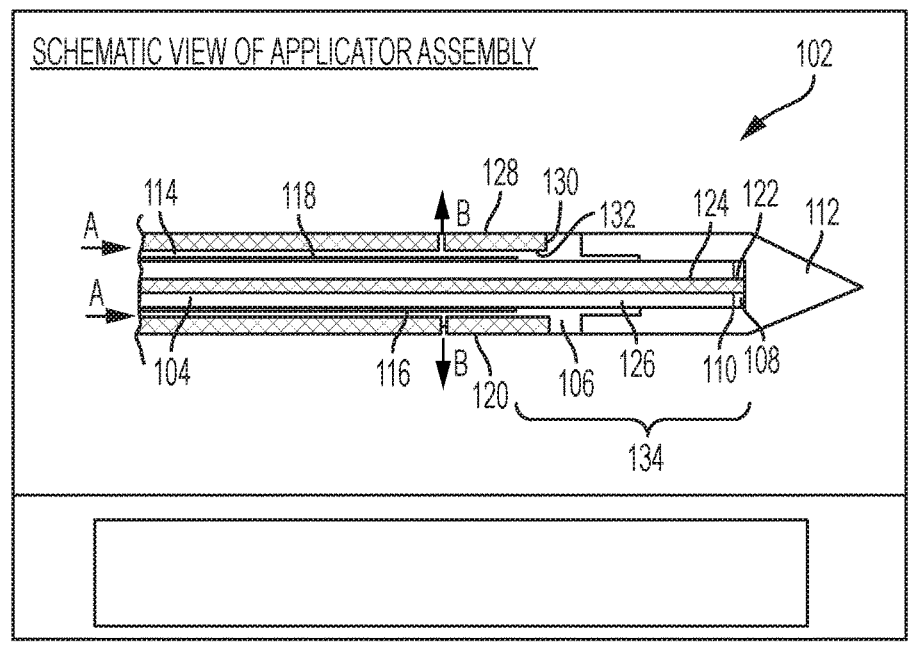
FIG. 1 is a schematic, partial cross-sectional view of a radiation applicator in accordance with one embodiment of the invention.

FIG. 1 is a schematic, partial cross-sectional view of a radiation applicator in accordance with one embodiment of the invention. The radiation applicator, generally designated 102, includes a distal end portion of a coaxial cable 104 that is used to couple to a source (not shown) of microwaves, a copper ferrule 106, a tuning washer 108 attached on the end 110 of the insulator part of the coaxial cable 104, and a tip 112. Preferably, the applicator 102 further includes a metal tube 114. Tube 114 is rigidly attached to the ferrule 106. An annular space 116 is defined between the outer conductor 118 of the cable 104 and the inner surface of the tube 114, enabling cooling fluid to enter (in the direction of arrows A), contact the heated parts of the applicator 102 and exit in the direction of arrows B through radial holes 120 in the tube 114, thereby extracting heat energy from the radiation applicator 102.

In assembly of the applicator 102, the washer 108 is soldered to a small length 122 of the central conductor 124 of the cable 104 that extends beyond the end 110 of the insulator 126 of the cable 104. The ferrule 106 is soldered to a small cylindrical section 128 of the outer conductor 118 of the cable 104. Then, the tube 114, which is preferably stainless steel, but may be made of other suitable materials, such as titanium or any other medical grade material, is glued to the ferrule 106 by means of an adhesive, such as Loctite 638 retaining compound, at the contacting surfaces thereof, indicated at 130 and 132. The tip 112 is also glued preferably, using the same adhesive, on the inner surfaces thereof, to corresponding outer surfaces of the ferrule 106 and the insulation 126.

When assembled, the applicator 102 forms a unitary device that is rigid and stable along is length, which may be of the order of 250 or so millimeters including tube 114, thereby making the applicator 102 suitable for insertion into various types of soft tissue. The space 116 and holes 120 enable cooling fluid to extract heat from the applicator 102 through contact with the ferrule 106, the outer conductor 118 of the cable 104 and the end of the tube 114. The ferrule 106 assists, among other things, in assuring the applicator's rigidity. The exposed end section 134 of cable 104 from which the outer conductor 118 has been removed, in conjunction with the dielectric tip 112, are fed by a source of radiation of predetermined frequency. The exposed end section 134 and dielectric tip 112 operate as a radiating antenna for radiating microwaves into tissue for therapeutic treatment. The applicator 102 operates as a dipole antenna, rather than a monopole device, resulting in an emitted radiation pattern that is highly beneficial for the treatment of certain tissues, such as malignant or tumorous tissue, due to its distributed, spherical directly heated area.

Figure 2B:
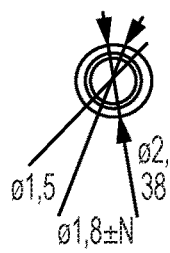
FIG. 2B shows an end elevation of the radiating tip of the radiation applicator of FIG. 1.
Figure 2A:
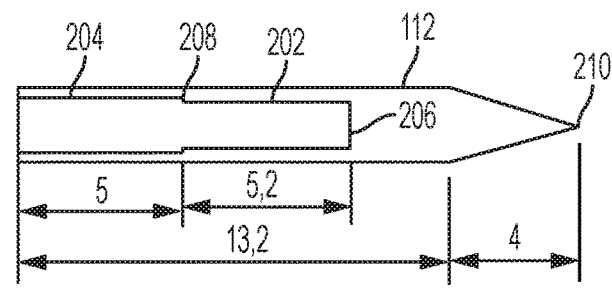
FIG. 2A shows an axial cross-section.

FIG. 2A shows an axial cross-section, and FIG. 2B shows an end elevation of the tip 112 of the radiation applicator 102 of FIG. 1. As can be seen, the tip 112 has inner cylindrical walls 202, 204, and abutting walls 206, 208, for receiving and abutting the washer 108 and the ferrule 106, respectively, during assembly. Suitably, the tip 112 is made of zirconia ceramic alloy. More preferably, it is a partially stabilized zirconia (PSZ) having yttria as the stabilizing oxidizing agent. Even more preferably, the tip 112 is made of Technox 2000, which is a PSZ commercially available from Dynamic Ceramic Ltd. of Staffordshire, England, having a very fine uniform grain compared to other PSZs, and a dielectric constant (k) of 25. As understood by those skilled in the art, the choice of dielectric material plays a part in determining the properties of the radiated microwave energy.

It will be noted that the transverse dimensions of the applicator 102 are relatively small. In particular, the diameter of applicator 102 is preferably less than or equal to about 2.4 mm. The tip 112, moreover, is designed to have dimensions, and be formed of the specified material, so as to perform effective tissue ablation at the operating microwave frequency, which in this case is preferably 2.45 Gigahertz (GHz). The applicator 102 of the present invention is thus well adapted for insertion into, and treatment of, cancerous and/or non-cancerous tissue of the liver, brain, lung, veins, bone, etc.

The end 210 of the tip 112 is formed by conventional grinding techniques performed in the manufacture of the tip 112. The end 210 may be formed as a fine point, such as a needle or pin, or it may be formed with an end blade, like a chisel, i.e. having a transverse dimension of elongation. The latter configuration has the benefit of being well suited to forcing the tip 112 into or through tissue, i.e., to perforate or puncture the surface of tissue, such as skin.

In use, the tip 112 is preferably coated with a non-stick layer such as silicone or paralene, to facilitate movement of the tip 112 relative to tissue.

Figure 3:
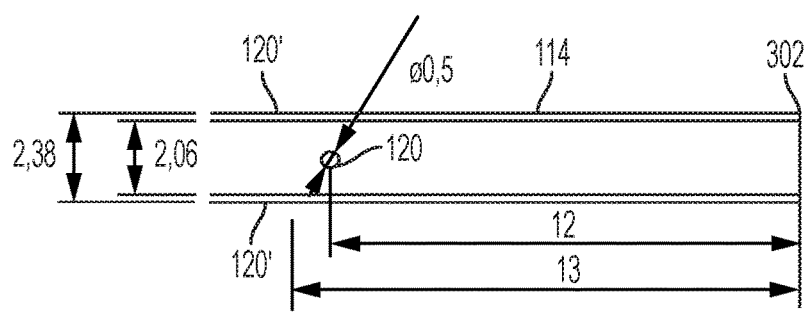
FIG. 3 shows a partial transverse cross-section of the tube of the radiation applicator of FIG. 1.

FIG. 3 shows a partial transverse cross-section of the tube 114. As mentioned above, the tube 114 is preferably made of stainless steel. Specifically, the tube 114 is preferably made from 13 gauge thin wall 304 welded hard drawn (WHD) stainless steel. The tube 114 is also approximately 215 mm in length. As can be seen, two sets of radial holes 120, 120' are provided at 12 mm and 13 mm, respectively, from the end 302 of the tube 114. These radial holes 120, 120', as mentioned, permit the exit of cooling fluid. Although two sets of holes are shown, one, three, four or more sets of holes may be provided, in variants of the illustrated embodiment. In addition, although two holes per set are shown, three, four, five, or more holes per set may be provided, so long as the structural rigidity of the tube 114 is not compromised. In this embodiment, the holes 120, 120' are of 0.5 mm diameter, but it will be appreciated that this diameter may be quite different, e.g. any thing in the range of approximately 0.1 to 6 mm, depending on the number of sets of holes and/or the number of holes per set, in order to provide an effective flow rate. Although the illustrated distance from the end 302 is 12 or 13 mm, in alternative embodiments, this distance may range from 3 mm to 50 mm from the end 302, in order to control the length of track that requires cauterization.

Further, in an embodiment used in a different manner, the tube 114 may be omitted. In this case the treatment may comprise delivering the applicator to the treatment location, e.g., to the tumorous tissue, by suitable surgical or other techniques. For example, in the case of a brain tumor, the applicator may be left in place inside the tumor, the access wound closed, and a sterile connector left at the skull surface for subsequent connection to the microwave source for follow-up treatment at a later date.

Figure 4A:
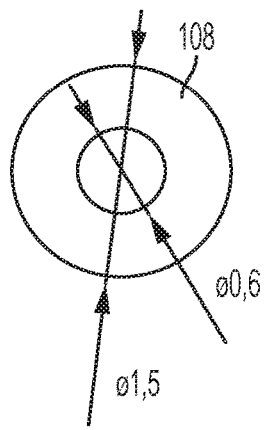
FIG. 4A shows a transverse cross-section.
Figure 4B:
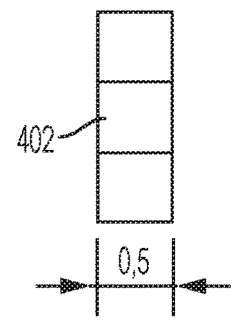
FIG. 4B shows an axial cross-section of the tuning washer of the radiation applicator of FIG. 1.

FIG. 4A shows a transverse cross-section, and FIG. 4B shows an axial cross-section of the tuning washer 108. The washer 108 is preferably made of copper, although other metals may be used. The washer 108 has an inner cylindrical surface 402 enabling it to be soldered to the central conductor 124 of the cable 104 (FIG. 1). Although the washer is small, its dimensions are critical. The washer 108 tunes the applicator 102, which operates as a dipole radiator, i.e., radiating energy from two locations, so that more effective treatment, i.e., ablation, of tissue is effected.

Figure 5B:
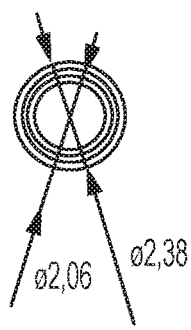
FIG. 5B shows an end elevation of the ferrule of the radiation applicator of FIG. 1.
Figure 5A:
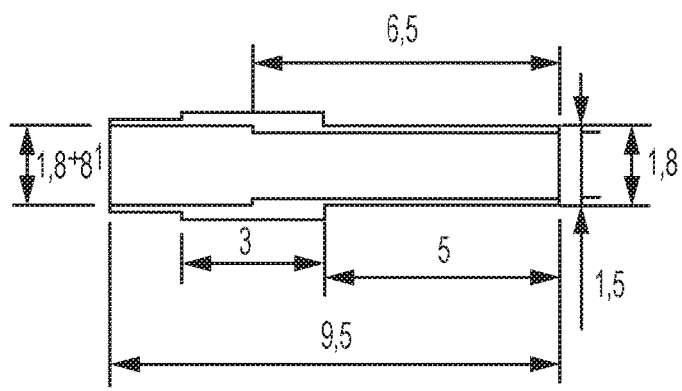
FIG. 5A shows an axial cross-section.

FIG. 5A shows an axial cross-section, and FIG. 5B shows an end elevation of the ferrule 106. The ferrate 106 is preferably made of copper, and is preferably gold plated to protect against any corrosive effects of the cooling fluid. The ferrule 106 may be produced by conventional machining techniques, such as CNC machining.

FIG. 6A shows an axial cross-section, and FIG. 6B shows a transverse cross-section at line B-B of a handle section 602 that may be attached to the tube 114 of the radiation applicator 102. The handle section 602 is preferably made from the same material as the tube 114, i.e., stainless steel. The handle section 602 includes a forward channel 604 enabling insertion of the tube 114, and a rear channel 606 enabling insertion of the coaxial cable 104 during assembly. A transverse port 608 having an internal thread 610 enables the connection, through a connector, to a source of cooling fluid, discussed later. The connector may be formed from plastic. Once assembled, the arrangement of handle section 602 enables cooling fluid to pass in the direction of arrow C into the tube 114 (not shown).

FIG. 7 illustrates the portion of coaxial cable 104 that passes through the tube 114. The cable 104 suitably comprises a low-loss, coaxial cable such as SJS070LL-253-Strip cable. A connector 702, preferably a SMA female type connector permits connection of the cable 104 to a microwave source (not shown), or to an intermediate section of coaxial cable (not shown) that, in turn, connects to the microwave source.

Figure 8:
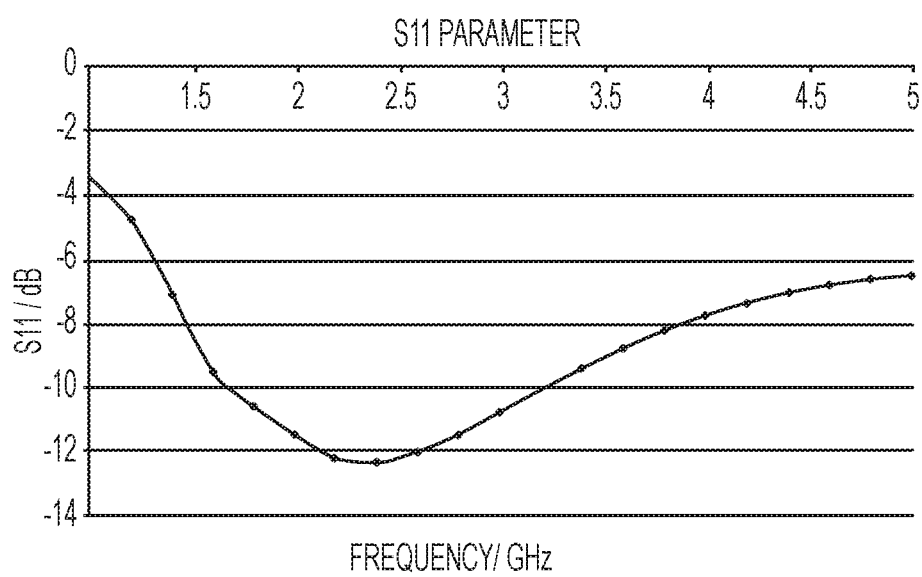
FIG. 8 is a plot of $S_{11}$ against frequency for the radiation applicator of FIG. 1.

FIG. 8 is a plot of S11 against frequency for the radiation applicator 102 of FIG. 1. This illustrates the ratio of reflective microwave power from the interface of the applicator 102 and treated tissue to total input power to the applicator 102. As can be seen, the design of the applicator 102 causes the reflected power to be a minimum, and therefore the transmitted power into the tissue to be a maximum, at a frequency of 2.45 GHz of the delivered microwaves.

Figure 9A:
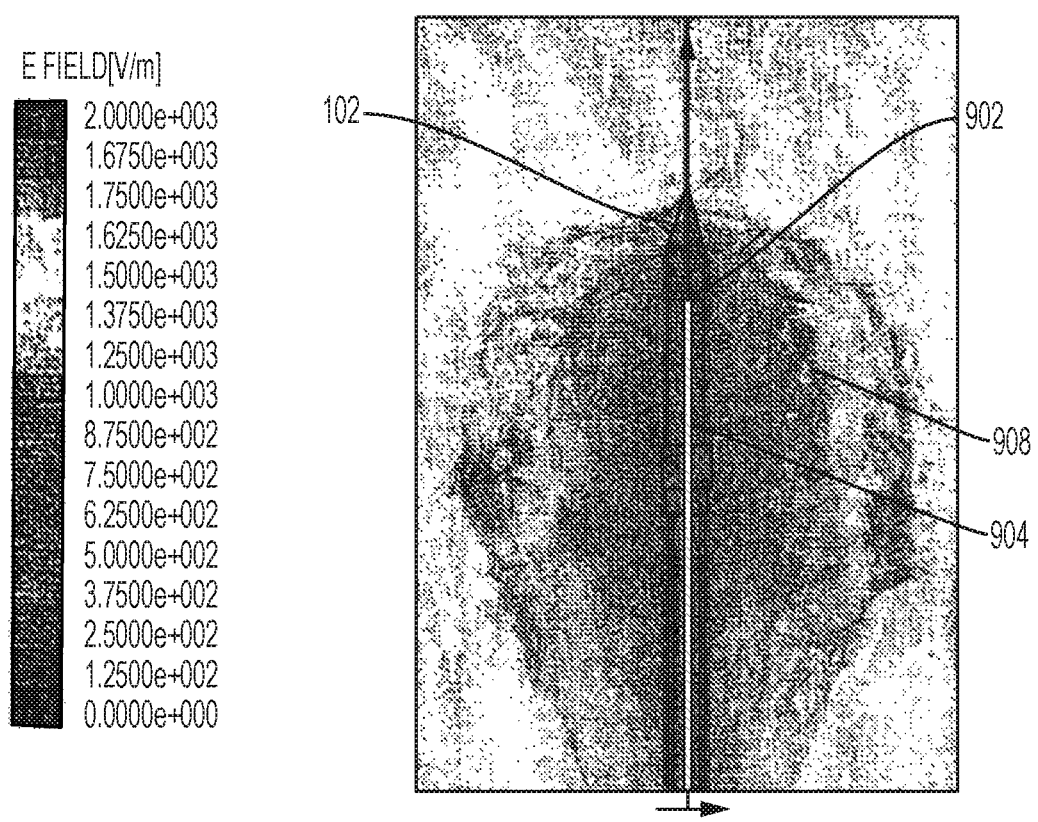
FIG. 9A illustrates the E-field distribution.

FIG. 9A shows the E-field distribution around the radiation applicator 102 of FIG. 1, in use. Darker colors adjacent to the applicator 102 indicate points of higher electric field.

In FIG. 9A the position of the washer 108 is indicated at 902, and the position of the tip-ferrule junction is indicated at 904. Two limited, substantially cylindrical zones 906, 908, of highest electric field are formed around the applicator 102 at the positions 902 and 904 respectively.

Figure 9B:
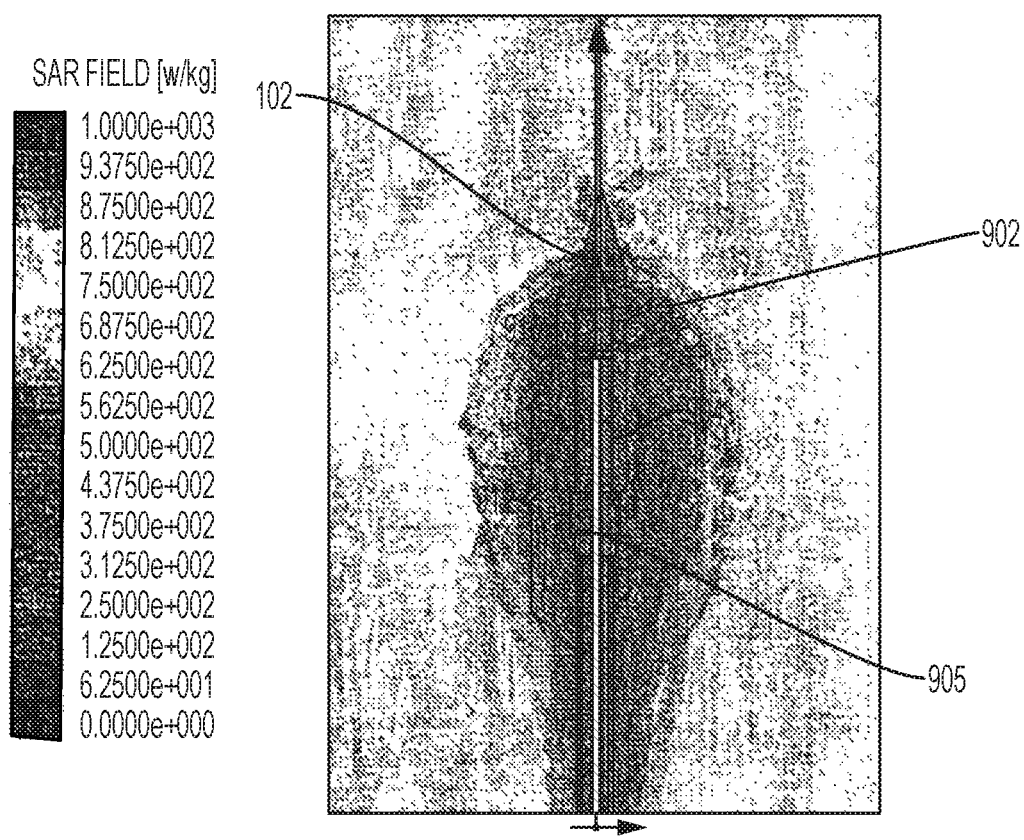
FIG. 9B illustrates the SAR values around the radiation applicator of FIG. 1, in use.

FIG. 9B shows the specific absorption rate (SAR) value distribution around the radiation applicator 102 of FIG. 1, in use. Darker colors adjacent the applicator 102 indicate points of SAR. In FIG. 9B, the position of the washer 108 is indicated at 902, the position of the tip-ferrule junction is indicated at 904, and the position of the ferrule-tube junction is indicated at 905. Two limited, substantially cylindrical zones 910, 912, of highest SAR are formed around the applicator 102 at the positions 902 and between 904 and 905, respectively.

Figure 10A:
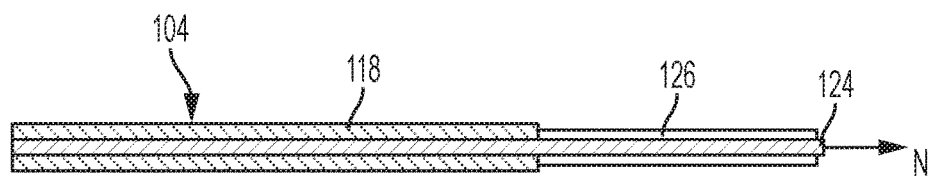
FIGS. 10A-E show a preferred sequential assembly of the radiation applicator of FIG. 1.

FIGS. 10A-E show a preferred sequential assembly of components forming the radiation applicator 102 of FIG. 1. In FIG. 10A, the coaxial cable 104 is shown with the outer conductor 118 and the inner insulator 126 trimmed back, as illustrated earlier in FIG. 7.

Figure 10B:
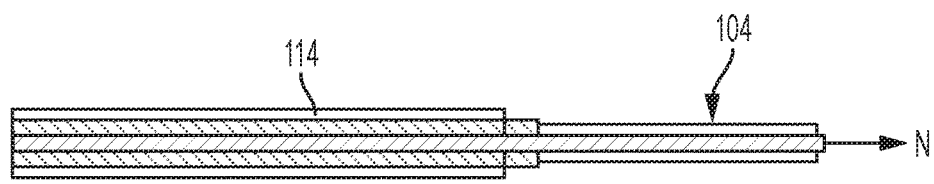
Figure 10C:
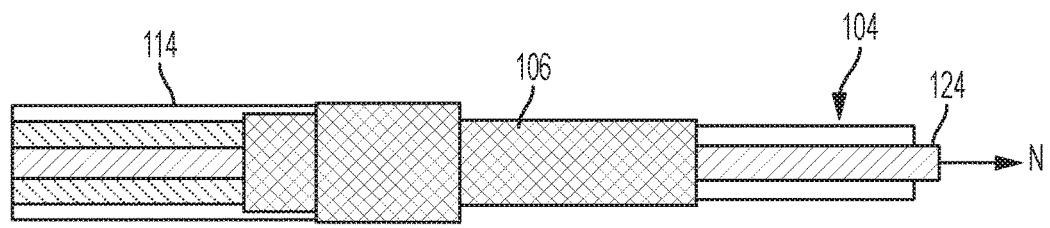
Figure 10D:
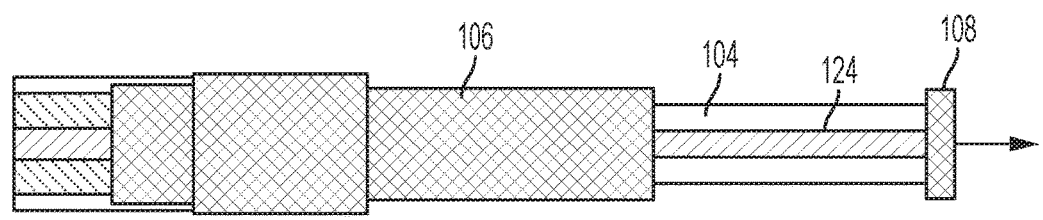
Figure 10E:
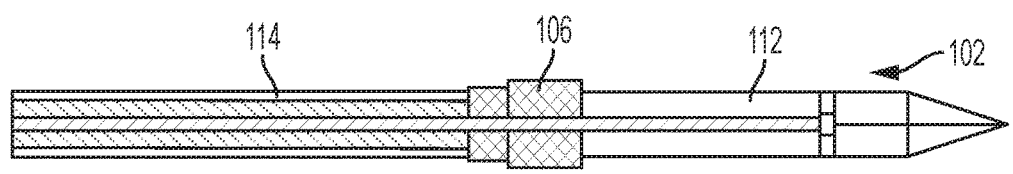

As shown in FIG. 10B, the tube 114 is then slid over the cable 104. Next, the ferrule rule 106 is slid over the cable 104 (FIG. 10C), and fixedly attached to the tube 114 and to the cable 104, as described earlier. Then, the washer 108 is attached to the inner conductor 124 by soldering, as shown in FIG. 10D. Finally, the tip 112 is slid over the cable 104 and part of the ferrule 106, and affixed thereto, as described earlier. The completed applicator is shown in FIG. 10E. This results in a construction of great rigidity and mechanical stability.

Figure 11:
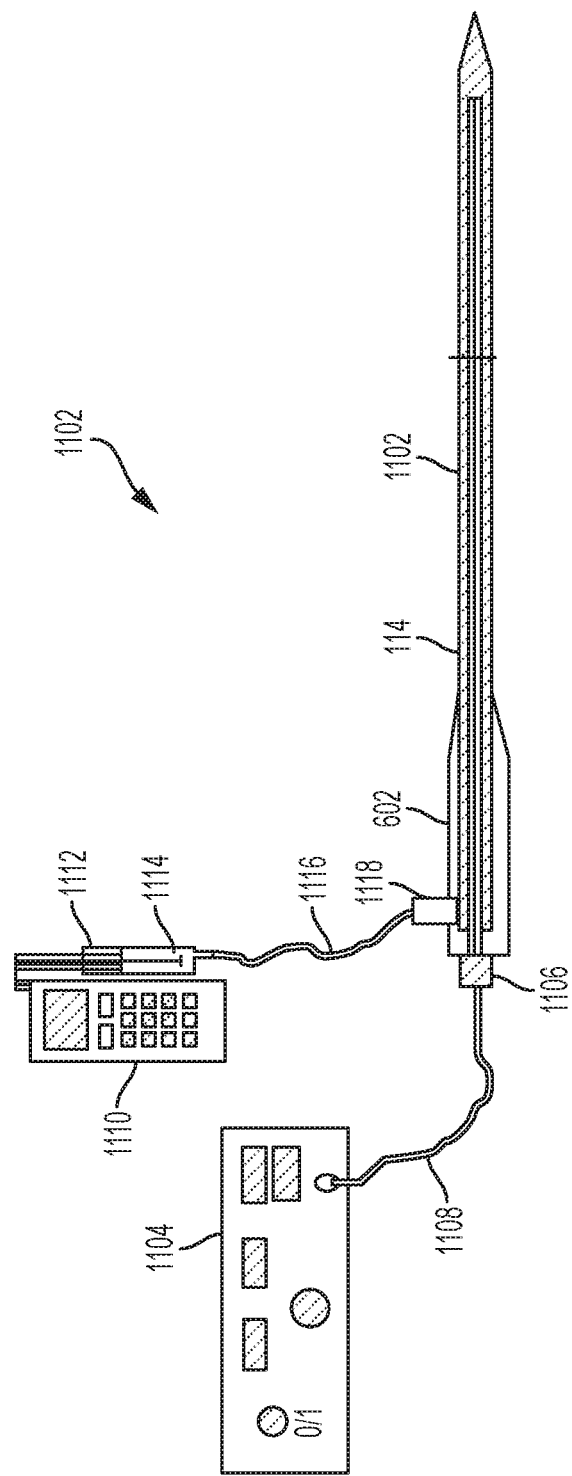
FIG. 11 schematically illustrates a treatment system employing the radiation applicator of FIG. 1.

FIG. 11 schematically illustrates a treatment system 1102 employing the radiation applicator 102 of FIG. 1. Microwave source 1104 is couple to the input connector 1106 on handle 602 by coaxial cable 1108. In this embodiment, the microwave power is supplied at up to 80 Watts. However this could be larger for larger size applicators, e.g., up to 200 Watts for 5 mm diameter radiation applicators.

Syringe pump 1110 operates a syringe 1112 for supplying cooling fluid 1114 via conduit 1116 and connector 1118 attached to handle 602, to the interior of the handle section 602. The fluid is not at great pressure, but is pumped so as to provide a flow rate of about 1.5 to 2.0 milliliter (ml)/minute through the pipe 114 in the illustrated embodiment. However, in other embodiments, where the radiation applicator 102 is operated at higher powers, higher flow rates may be employed, so as to provide appropriate cooling. The cooling fluid is preferably saline, although other liquids or gases may be used, such as ethanol. In certain embodiments, a cooling liquid having a secondary, e.g., cytotoxic, effect could be used, enhancing the tumor treatment. In the illustrative embodiment, the cooling fluid 1114 exits the tube 114, as shown by arrows B in FIG. 1, at a temperature on the order of 10° C. higher than that at which it enters the tube 114, as shown by arrows A in FIG. 1. Thus, substantial thermal energy is extracted from the coaxial cable. The cooling fluid 1114 may, for example, enter the tube 114 at room temperature. Alternatively, the cooling fluid 1114 may be pre-cooled to a temperature below room temperature by any suitable technique.

As shown, the cooling system is an open, perusing totaling system that cools the coaxial cable connected to the radiation applicator 102. That is, after absorbing heat from the coaxial cable, the cooling fluid perfuses the tissue near the radiation applicator 102.

The methodology for use of the radiation applicator 102 of the present invention may be as conventionally employed in the treatment of various soft tissue tumors. In particular, the applicator 102 is inserted into the body, laparoscopically, percutaneously or surgically. It is then moved to the correct position by the user, assisted where necessary by positioning sensors and/or imaging tools, such as ultrasound, so that the tip 112 is embedded in the tissue to be treated. The microwave power is switched on, and the tissue is thus ablated for a predetermined period of time under the control of the user. In most cases, the applicator 102 is stationary during treatment. However, in some instances, e.g., in the treatment veins, the applicator 102 may be moved, such as a gentle sliding motion relative to the target tissue, while the microwave radiation is being applied.

As described above, and as shown in FIGS. 9A and 9B, radiation applicator 102, is a dipole antenna. The portion of the inner conductor 124 that extends beyond the ferrule 106 operates as one arm of the dipole antenna. In addition, the transmission of microwave energy along the inner conductor 124 and in the aperture of the ferrule induces a current to flow on that portion of the outer surface of the ferrule 106 that is located underneath the tip 112. This induced current causes this enclosed, outer surface of the ferrule 106 to emit microwave radiation, thereby forming a second arm of the dipole antenna. The bipolar configuration of the applicator effectively spreads the microwave radiation that is being transmitted by the applicator 102 along a greater transverse, i.e., axial, length of the antenna 102, rather than focusing the radiation transmission solely from the tip 112 of the applicator 102. As a result, the applicator 102 of the present invention may be operated at much higher power levels, e.g., up to approximately 80 Watts, than prior art designs.

Figure 12:
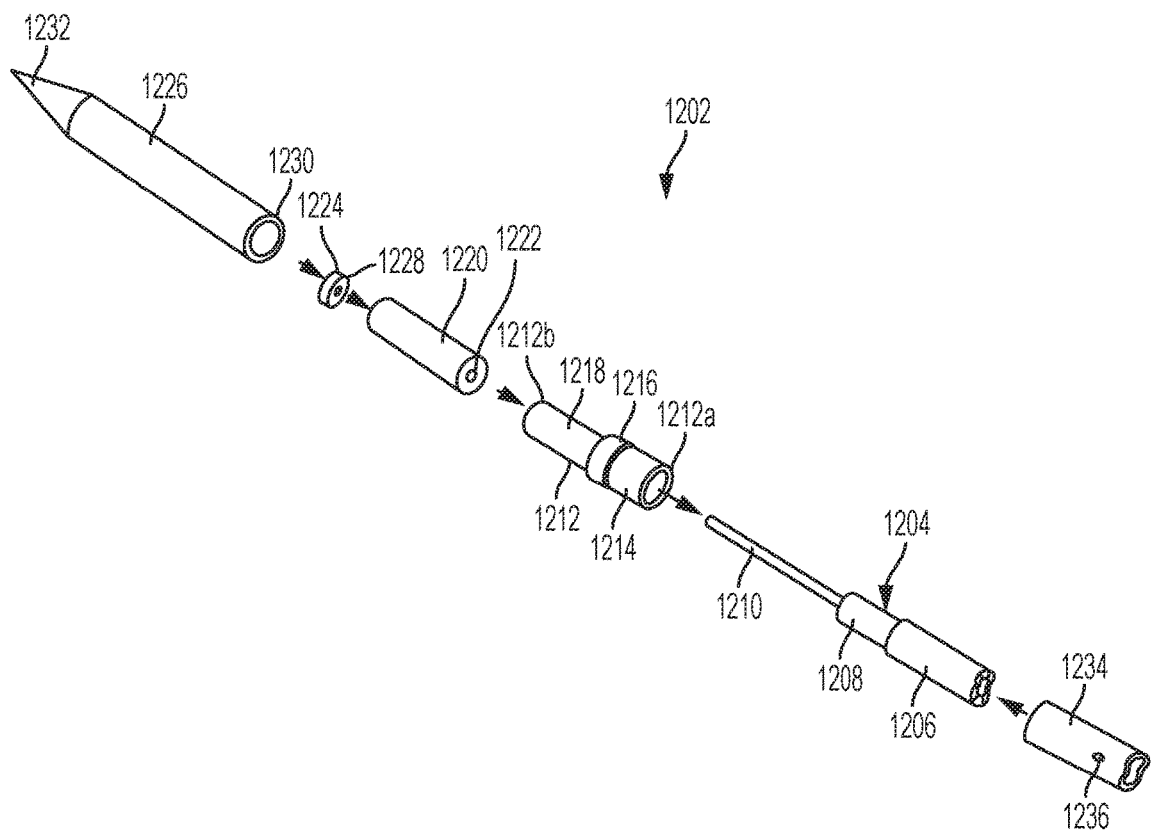
FIG. 12 is an exploded, perspective view of another embodiment of the present invention.

An alternative embodiment of the present invention is shown in FIGS. 12-19. FIG. 12 is an exploded, perspective view of an alternative radiation applicator 1202. As shown, the applicator 1202 includes a coaxial cable 1204 having an outer conductor 1206 that surrounds an insulator 1208 that, in turn, surrounds an inner or central conductor 1210. The applicator 1202 further includes a ferrule 1212. The ferrule 1212 is generally tubular shaped so as to define an aperture therethrough, and has first and second ends 1212a, 1212b. The ferrule 1212 also has three parts or sections. A first section 1214 of the ferrule 1212 has an inner diameter sized to fit over the outer conductor 1206 of the coaxial cable 1204. A second section 1216 of the ferrule 1212 has an inner diameter that is sized to fit over the insulator 1208 of the coaxial cable 1204. The second section 1216 thus defines an annular surface or flange (not shown) around the inside the ferrule 1212. The outer diameter of the second section 1216 is preferably larger than the outer diameter of the first section 1214, thereby defining a step or flange around the outside of the ferrule 1212. A third section 1218 of the ferrule 1212 has an inner diameter also sized to fit around the insulator 1208 of the coaxial cable 1204. The third section 1218 has an outside diameter that is less than the outside diameter of the second section 1216. The third section 1218 this defines an outer, cylindrical surface or sleeve.

Applicator 1202 further includes a spacer 1220. The spacer 1220 is preferably cylindrical in shape with a central bore 1222 sized to receive the inner conductor 1210 of the coaxial cable 1204. The outer diameter of the spacer 1220 preferably matches the outer diameter of the third section 1218 of the ferrule 1212. Applicator 1202 also includes a tuning element 1224 and a tip 1226. The tuning element 1224, which be may be disk-shaped, has a central hole 1228 sized to it around the inner conductor 1210 of the coaxial cable 1204. The tip 1226 is a hollow, elongated member, having an open end 1230, and a closed end 1232. The closed end 1232 may be formed into a cutting element, such as a trocar point or a blade, to cut or pierce tissue. Applicator 1202 also includes a rigid sleeve 1234. The sleeve 1234 has an inner diameter that is slightly larger than outer diameter of the coaxial cable 1204. As described below, an annular space is thereby defined between the outer surface of the coaxial cable 1204 and the inner surface of the sleeve 1234. The sleeve 1234 further includes one or more drainage holes 1236 that extend through the sleeve.

Figure 13:
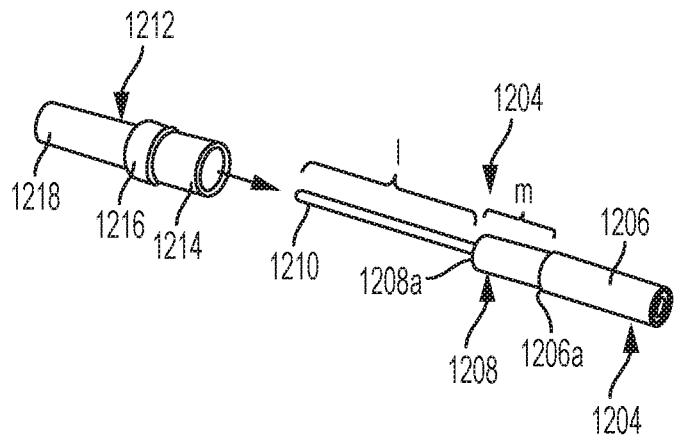
FIGS. 13-18 show a preferred sequential assembly of the radiation applicator of FIG. 12.
Figure 14:
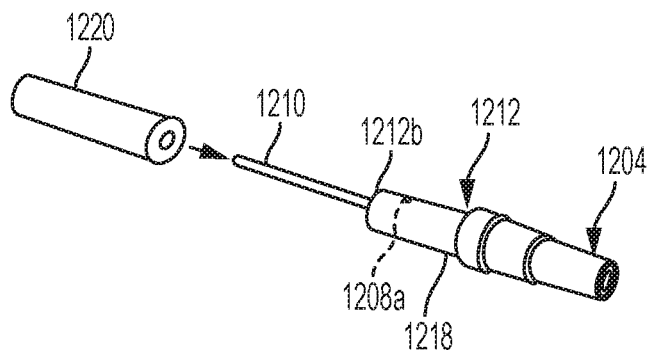
Figure 15:
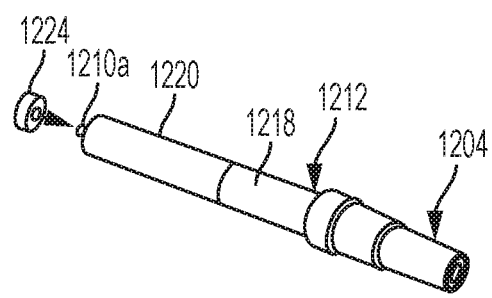

FIGS. 13-18 illustrate a preferred assembly sequence of the applicator 1202. As shown in FIG. 13, the coaxial cable 1204 is trimmed so that there is a length "m" of insulator 1208 that extends beyond an end 1206*a* of the outer conductor 1206, and a length "l" of inner conductor 1210 that extends beyond an end 1208*a* of the insulator 1208. The ferrule 1212 slides over the exposed inner conductor 1210 and over the exposed insulator 1208 such that the first section 1214 surrounds the outer conductor 1206, and the second and third sections 1216, 1218 surround the exposed portion of the insulator 1208. The inner surface or flange formed on the second section 1216 of the ferrule 1212 abuts the end 1206*a* of the outer conductor 1206, thereby stopping the ferrule 1212 from sliding any further up the coaxial cable 1204. The ferrule 1212 is preferably fixedly attached to the coaxial cable 1204, such as by soldering the ferrule 1212 to the outer conductor 1206 of the coaxial cable 1204. In the preferred embodiment, the third section 1218 of the ferrule 1212 extends past the end 1208*a* of the exposed insulator 1208 as shown by the dashed line in FIG. 14.

Next, the spacer 1220 is slid over the exposed portion of the inner conductor 1210, and is brought into contact with the second end 1212*b* of the ferrule 1212. In the preferred embodiment, the spacer 1220 is not fixedly attached to the ferrule 1212 or the inner conductor 1210. The spacer 1220 is sized so that a small portion 1210*a* (FIG. 15) of the inner conductor 1210 remains exposed. The tuning element 1224 is then slid over this remaining exposed portion 1210*a* of the inner conductor 1210. The tuning element 1224 is preferably fixedly attached to the inner conductor 1210, e.g., by soldering. The timing element 1224, in cooperation with the ferrule 1212, thus hold the spacer 1220 in place.

Figure 16:
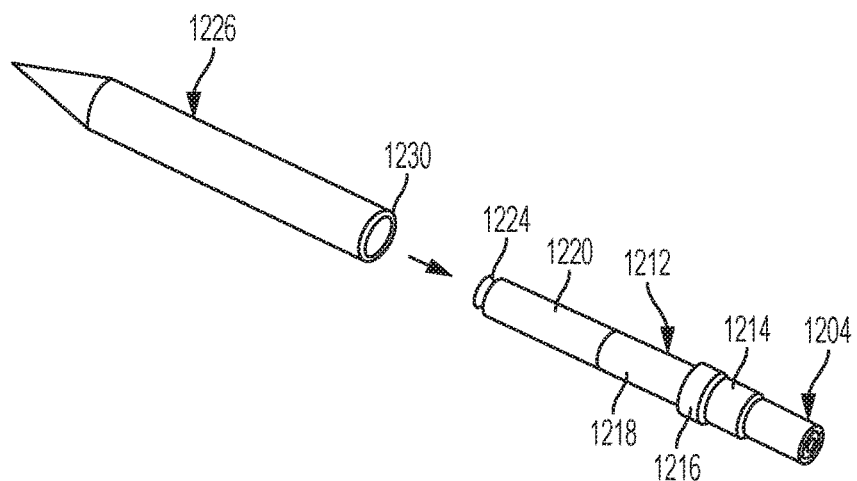
Figure 17:
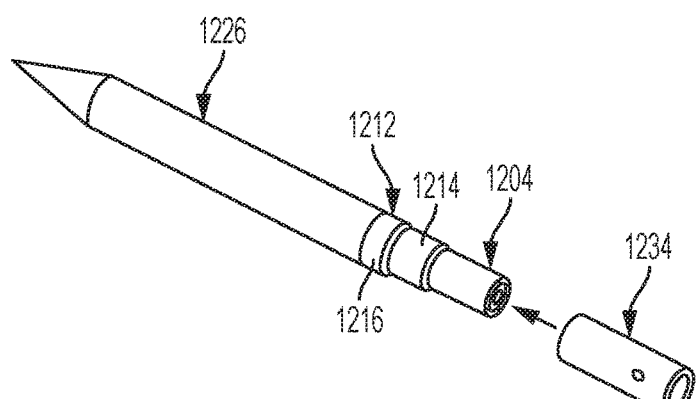

With the tuning element 1224 in place, the next step is to install the tip 1226 as shown in FIG. 16. The open end 1230 of the tip 1226 is slid over the tuning element 1224, the spacer 1224 and the third section 1218 of the ferrule 1212. The open end 1230 of the tip 1226 abuts the second section or step 1216 of the ferrule 1212. The tip 1226 is preferably fixedly attached to the ferrule 1212, e.g., by bonding. With the tip 1226 in place, the next step is to install the sleeve 1234 (FIG. 17). The sleeve 1234 is slid over the coaxial cable 1234, and up over the first section 1214 of the ferrule 1212. The sleeve 1234 abuts the step 1216 in the ferrule 1212 opposite the tip 1226.

Those skilled in the art will understand that the applicator 1202 may be assembled in different ways or in different orders.

Figure 18:
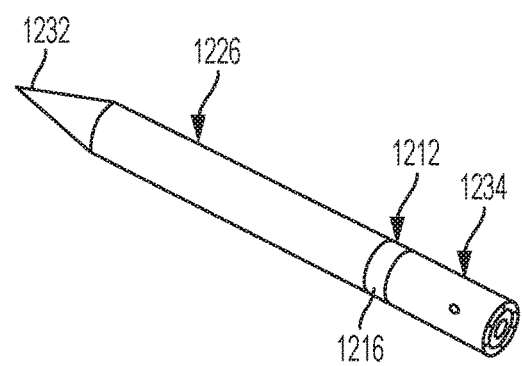

As illustrated in FIG. 18, upon assembly, the tip 1226, second section 1216 of the ferrule 1212, and sleeve 1234 all preferably have the same outer diameter, thereby giving the applicator 1202 a smooth outer surface.

Preferably, the sleeve 1234 is formed from stainless steel, and the ferrule 1212 is formed from gold-plated copper. The tip 1226 and the spacer 1220 are formed from dielectric materials. In the illustrative embodiment, the tip 1226 and the spacer 1220 are formed from an itrium stabilized zirconia, such as the Technox brand of ceramic material commercially available from Dynamic Ceramic Ltd. of Stoke-on-Trent, Staffordshire, England, which has a dielectric constant of 25. The tip 1226 may be further provided with a composite coating, such as a polyimide undercoat layer, for adhesion, and a paralyne overcoat layer, for its non-stick properties. Alternatively, silicone or some other suitable material could be used in place of paralyne. The composite coating may also be applied to the ferrule and at least part of the stainless steel sleeve, in addition to being applied to the tip.

Those skilled in the art will understand that alternative materials may be used in the construction of the radiation applicator 1202.

Figure 19:
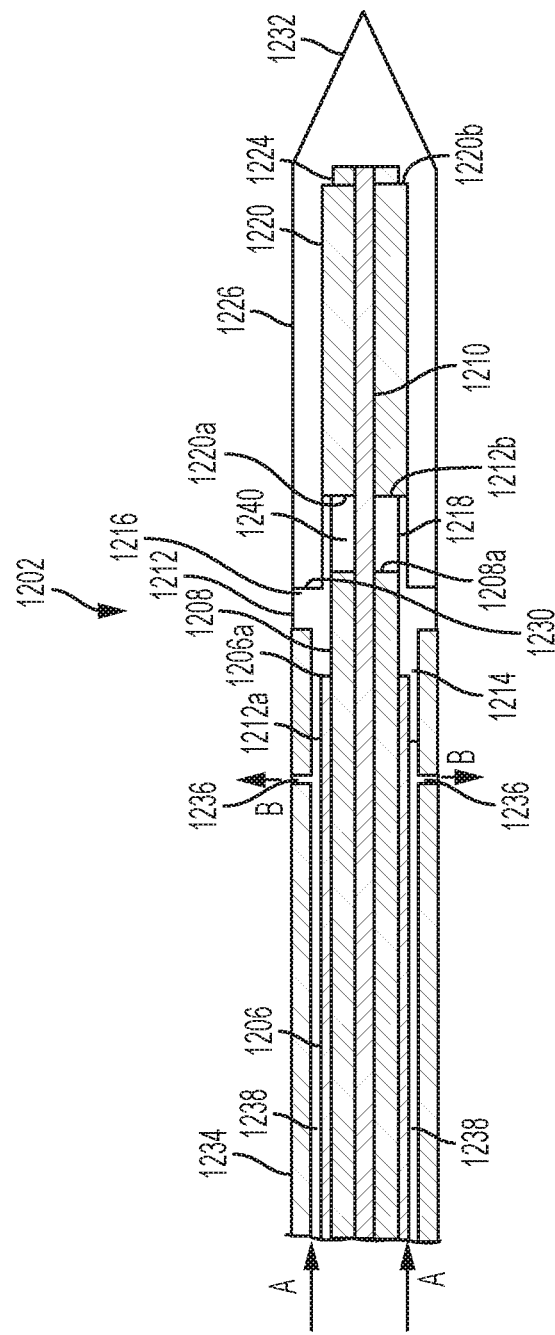
FIG. 19 is a schematic, partial cross-sectional view of the radiation applicator of FIG. 12.

FIG. 19 is a schematic, partial cross-sectional view of the radiation applicator 1202. As shown, at least part of the first section 1214 of the ferrule 1212 overlies and is attached to the outer conductor 1206. The insulator 1208 extends partially through the inside of the ferrule 1212. In particular, the end 1208*a* of the insulator 1208 is disposed a predetermined distance back from the second end 1212*b* of the ferrule 1212. The inner conductor 1210 extends completely through and beyond the ferrule 1212. The sleeve 1234 slides over and is bonded to the first section 1214 of the ferrule 1212. As shown, the inside diameter of the sleeve 1234 is greater than the outside diameter of the coaxial cable 1204, thereby defining an annular space 1238 between the outside of the coaxial cable 1204 and the inside of the sleeve 1234. Cooling fluid, such as saline, is pumped through this annular space 1238, as shown by arrows A. The cooling fluid absorbs heat from the coaxial cable that feeds radiation to applicator 1202. The cooling fluid is then discharged through holes 1236 in the sleeve 1234, as shown by arrows B.

In the preferred embodiment, the holes 1236 are placed far enough behind the closed end 1232 of the tip 1226 such that the discharged cooling fluid does not enter that portion of the tissue that is being heated by the radiation applicator 1202. Instead, the discharged cooling fluid preferably perfuses tissue outside of this heated region. Depending on the tissue to be treated, a suitable distance between the closed end 1232 of the tip 1226 and the holes 1236 may be approximately 30 mm.

A first end 1220*a* of the spacer 1220 abuts the second end 1212*b* of the ferrule 1212, while a second end 1220*b* of the spacer 1220 abuts the tuning element 1224. Accordingly a space, designated generally 1240, is defined within the ferrule 1212 between the end 1208*a* of the insulator and the second end 1212*b* of the ferrule. In the illustrative embodiment, this space 1240 is filled with air. Those skilled in the art will understand that the space may be filled with other materials, such as a solid dielectric, or it may be evacuated to form a vacuum. The inside surface of the tip 1226 preferably conforms to the shape of the tuning element 1224, the spacer 1220, and the third section 1218 of the ferrule 1212 so that there are no gaps formed along the inside surface of the tip 1226.

As indicated above, operation of the radiation applicator 1202 pauses a current to be induced on the outer surface of the third section 1218 of the ferrule 1212, which is enclosed within the dielectric material of the tip 1226. This induced current results in microwave energy being radiated from this surface of the ferrule 1212, thereby forming one arm of the dipole. The section of the inner conductor 1210 that extends beyond the ferrule 1212 is the other arm of the dipole. Both the length of the inner conductor 1210 that extends beyond the ferrule 1212, and the length of the third section 1218 of the ferrule 1212, which together correspond to the two arms of the dipole, are chosen to be approximately ¼ of the wavelength in the dielectric tip 1226, which in the illustrative embodiment is approximately 6 mm. Nonetheless, those skilled in the art will understand that other factors, such as tissue permittivity, the action of the tuning element, etc., will affect the ultimate lengths of the dipole arms. For example, in the illustrative embodiment the two arms are approximately 5 mm in length.

The tuning element 1224, moreover, cooperates with the second section or step 1216 of the ferrule to balance the radiation, being emitted by the two arms of the dipole. In particular, the size and shape of the tuning element 1224 and the step 1216 are selected such that the coherent sum of the microwave power reflected back toward the cable at the aperture of the ferrule is minimized. Techniques for performing such design optimizations are well-known to those skilled in the relevant art.

In use, the radiation applicator 1202 is attached to a source of microwave radiation in a similar manner, as described above in connection with the applicator 102 of FIG. 1. The coaxial cable is also attached to a source of cooling fluid in a similar manner as described above. With the present invention, it is the dielectric tip, ferrule and stainless steel sleeve that cooperate to provide the necessary stiffness and mechanical strength for the applicator to be used in treatment procedures. The applicator does not rely on the coaxial cable for any of its strength. Indeed, a flexible coaxial cable, having little or no rigidity, could be used with the radiation applicator of the present invention.

The foregoing has been a detailed description of illustrative embodiments of the invention. Various modifications and additions can be made without departing from the spirit and scope thereof. For example, the materials described herein are not exhaustive, and any acceptable material can be employed for any component of the described system and method. In addition, modifications can be made to the shape of various components. Accordingly, this description is meant to be taken only by way of example, and not to otherwise limit the scope of the invention.

What is claimed is:

1. A method of treating tissue, the method comprising:
   inserting into the body a radiation applicator for applying electromagnetic radiation to tissue, the radiation applicator comprising:
   a central conductor having a distal end and a proximal end, an outer conductor having a distal end and a proximal end, the outer conductor also having an inner surface and an outer surface;
   an outer tube having a proximal end and a distal portion, the distal portion including a distal most end, the outer tube also having an inner surface and an outer surface, the distal most end of the outer tube ending proximal to a distal most end of the applicator, the outer tube coaxially surrounding the outer conductor such that a gap is formed between the outer surface of the outer conductor and the inner surface of the outer tube;
   a dielectric tip member;
   a ferrule having a proximal end and a distal end portion including a distal most end, the distal most end of the ferrule extending distally beyond the distal most end of the outer tube for a selected distance, the ferrule having a first surface, second surface, and a third surface, the first surface of the ferrule extending coaxially along the outer conductor and the central conductor, the second surface of the ferrule coaxially extends between the distal end of the outer conductor and the distal end of the outer tube, and the third surface of the ferrule coaxially extends along the distal end of the central conductor, the ferrule is spaced between the outer conductor and the outer tube thereby sealing the gap such that the proximal end of the ferrule prevents a cooling fluid from contacting a dipole antenna;
   a tuning conductor attached to the distal end of the central conductor, the tuning conductor is in electrical contact with the central conductor; and
   a dipole antenna formed by the tuning conductor and the dielectric tip member, the dipole antenna configured to radiate electromagnetic energy in at least a radial direction from the dielectric tip member;
   placing the dielectric tip in the tissue to be treated;
   powering on the energy source;
   delivering the energy to the tissue; and
   withdrawing the radiation applicator.

2. The method of claim 1, wherein the radiation applicator further comprises the first surface of the ferrule being proximal to the second surface of the ferrule and the second surface of the ferrule being proximal to the third surface of the ferrule.

3. The method of claim 1, wherein the radiation applicator further comprises an insulator coaxially extending between the central conductor and outer conductor, the insulator extending a selected distance beyond the distal most end of the outer conductor.

4. The method of claim 2, wherein the radiation applicator further comprises a proximal most end of the ferrule is a selected distance proximal to the distal most end of the outer conductor.

5. The method of claim 1, wherein the radiation applicator further comprises a tuning conductor received by an abutment wall of the distal end of the central conductor.

6. The method of claim 5, wherein the tuning conductor of the radiation applicator is a metal washer.

7. The method of claim 1, wherein the radiation applicator further comprises a connector for connecting the applicator to an energy source.

8. The method of claim 1, wherein the radiation applicator further comprises an antenna that is capable of creating a frequency of up to 8 GHz.

9. The method of claim 1, wherein the target tissue being treated is a tumor or other soft tissue.

10. A method of treating tissue, the method comprising:
    inserting into the body a radiation applicator for applying electromagnetic radiation to tissue, the radiation applicator comprising:
    a central conductor having a distal end and a proximal end, an outer conductor having a distal end and a proximal end, the outer conductor also having an inner surface and an outer surface;
    an outer tube having a proximal end and a distal portion, the distal portion including a distal most end, the outer tube also having an inner surface and an outer surface, the distal most end of the outer tube ending proximal to a distal most end of the applicator, the outer tube coaxially surrounding the outer conductor such that a gap is formed between the outer surface of the outer conductor and the inner surface of the outer tube;
    a dielectric tip member;
    a ferrule having a proximal end and a distal end portion including a distal most end, the distal most end of the ferrule extending distally beyond the distal most end of the outer tube for a selected distance, the ferrule having a first surface, second surface, and a third surface, the first surface of the ferrule extending coaxially along the outer conductor and the central conductor, the second surface of the ferrule coaxially extends between the distal end of the outer conductor and the distal end of the outer tube, and the third surface of the ferrule coaxially extends along the distal end of the central conductor, the ferrule is spaced between the outer conductor and the outer tube thereby sealing the gap such that the proximal end of the ferrule prevents a cooling fluid from contacting a dipole antenna;

a tuning conductor attached to the distal end of the central conductor, the tuning conductor is in electrical contact with the central conductor; and a dipole antenna formed by the tuning conductor and the dielectric tip member, the dipole antenna configured to radiate electromagnetic energy in at least a radial direction from the dielectric tip member;

placing the dielectric tip in the tissue to be treated;

flowing fluid through the gap but not beyond the ferrule;

powering on the energy source;

delivering the energy to the tissue; and withdrawing the radiation applicator.

11. The method of claim 10, wherein the applicator further comprises the first surface of the ferrule being proximal to the second surface of the ferrule and the second surface of the ferrule being proximal to the third surface of the ferrule.

12. The method of claim 11, wherein the applicator further comprises a proximal most end of the ferrule being a selected distance proximal to the distal most end of the outer conductor.

13. The method of claim 10, wherein the flowing fluid step further comprises:

a fluid conduit connected to a source of fluid via a pumping device, the pumping device flows fluid at a predetermined rate.

14. The method of claim 13, wherein the flowing fluid step further comprises fluid being pumped so as to provide a flow rate of at least 1.5 ml/minute.

15. The method of claim 13, wherein the flowing fluid step further comprises the fluid being at room temperature or pre-cooled to a temperature below room temperature.

16. The method of claim 13, wherein the flowing fluid step further comprises flow of fluid being stopped proximate to the dipole antenna.

17. The method of claim 10, wherein the radiation applicator further comprises a tuning conductor received by an abutment wall of the distal end of the central conductor.

18. The method of claim 10, wherein the radiation applicator further comprises a connector for connecting the applicator to an energy source.

19. The method of claim 10, wherein the radiation applicator further comprises an antenna that is capable of creating a frequency of up to 8 GHz.

20. The method of claim 10, wherein the target tissue being treated is a tumor or other soft tissue.

* * * * *